United States Patent [19]

Drury

[11] 4,231,941
[45] Nov. 4, 1980

[54] SYNTHESIS OF 2,5-DIHYDROFURAN

[75] Inventor: Robert F. Drury, Hightstown, N.J.

[73] Assignee: E. I. Du Pont de Nemours and Company, Wilmington, Del.

[21] Appl. No.: 51,972

[22] Filed: Jun. 25, 1979

[51] Int. Cl.³ .................................. C07D 307/28
[52] U.S. Cl. .................................. 260/346.11
[58] Field of Search .................................. 260/346.11

[56] References Cited
U.S. PATENT DOCUMENTS
3,812,158   5/1974   Besozzi et al. .................. 260/346.11

Primary Examiner—Richard Raymond

[57] ABSTRACT

Improved process for preparing 2,5-dihydrofuran by the dehydration of 1-butene-3,4-diol in the presence of a soluble mercury salt as catalyst in a dissociating solvent at a neutral or acidic pH at an elevated temperature, the improvement characterized in that the dehydration is carried out at a pH of 4 to 7 at 80°–120° C. in the presence of solid mercuric oxide.

9 Claims, No Drawings

SYNTHESIS OF 2,5-DIHYDROFURAN

DESCRIPTION

TECHNICAL FIELD

This invention relates to the preparation of 2,5-dihydrofuran from 1-butene-3,4-diol.

One object of this invention is to provide a catalytic process for preparing 2,5-dihydrofuran from 1-butene-3,4-diol in yields which are substantially better than those achieved by means of similar prior art processes. Another object is to provide such a process which exhibits higher conversions, than similar prior art processes, of the diol starting material. Still another object is to provide such a process which minimizes the amounts of by-products formed, as compared to similar prior art processes. Other objects will become apparent hereinafter.

BACKGROUND

The dehydration of alkane- and alkenediols to cyclic ethers is well known in the art. The reaction can be carried out in the presence or absence of a homogeneous or heterogeneous catalyst, usually an acidic catalyst. It is known, for example, that butane- and butenediols can be dehydrated to furan and/or partially and/or completely saturated furans, such as 2,3-dihydrofuran, 2,5-dihydrofuran and tetrahydrofuran. Catalysts known in the art for such dehydrations include organic and inorganic acids, such as sulfuric and hydrochloric acids, $Na_2Cr_2O_7/H_2SO_4$, pyridine hydrochloride and salts providing halide ions, water-insoluble metal oxides and salts, for example, oxides of Al, Ti, Zr and Th, neutral phosphates of Al, Fe, Ce, Ag and U, silica gel, bleaching earths and acid-type heterogeneous materials, such as aluminas and alumino-silicates. Typical of the art of such dehydrations of butenediol in Ind. Eng. Chem. Prod. Res. Develop., Vol. 12, No. 3, 1973, page 184 wherein is disclosed a study of the dehydration of 2-butene-1,4-diol using acid-type catalysts. The major products of the dehydration are disclosed to be 2,5-dihydrofuran, crotonaldehyde and furan.

U.S. Pat. No. 3,812,158 discloses the preparation of 2,5-dihydrofuran from 3,4-epoxy-1-butene, 3,4-dihydroxy-1-butene or 1,4-dihydroxy-2-butene, in yields of about 15 to 35%, using a soluble mercury salt in a neutral or acidic hydroxylic solvent in the liquid phase at 5°–150° C. Soluble mercury salts include mercury (II) sulfate, chloride, acetate, nitrate, chromate and fulminate and mercury (I) chlorate, chromate and acetate. Other useful mercury compounds include those which can be converted to a soluble salt in the solvent or a component of the solvent, for example, mercury (II) oxide which can be converted to the soluble sulfate by means of sulfuric acid.

DISCLOSURE OF INVENTION

For further comprehension of the invention and of the objects and advantages thereof reference may be made to the following description and to the appended claims in which the various novel features of the invention are more particularly set forth.

The invention resides in an improved process for preparing 2,5-dihydrofuran by dehydrating 1-butene-3,4-diol in the presence of a soluble mercury salt as catalyst in a dissociating solvent at a neutral or acidic pH at an elevated temperature, the improvement characterized in that the dehydration is carried out batchwise or continuously at a pH of 4 to 7, measured in an aqueous system, at 80°–120° C., preferably at reflux temperature, in the presence of solid mercury (II) oxide.

Aqueous solutions of soluble mercury salts of strong acids have a pH of the order of one; when solid mercuric oxide is present, the pH is in the range 4–7. The mercuric oxide, in solid form, is believed to prevent the reaction medium from becoming to acidic that unwanted side reactions occur, but it does not decrease the requisite high concentration of mercury ions in solution. Accordingly, high yields, which depend on relatively low pH, and high rates, which depend on high mercuric ion concentration, are both favored.

The presence of solid mercuric oxide offers a further advantage in that it neutralizes any acid formed by unwanted side reactions. This acid is generated by the reaction of some of the mercury ions in solution with organic compounds in the reaction mixture. For example, dihydrofuran reacts with mercuric ion to give metallic mercury, furan and hydrogen ions. The acid thus formed, which normally is detrimental to the process, is neutralized by reaction with the solid mercuric oxide, thus regenerating mercury ions. By means of this invention, therefore, the acidity of the reaction medium is controlled without introduction or formation of any foreign substance, such as another acidic compound, a phosphate or a $BF_3$-ether complex, which might make subsequent product separation and purification of the desired product more difficult. If the process is carried out continuously, any metallic mercury which is formed can be drawn off, reoxidized to mercuric oxide by known methods and reused.

Although any dissociating solvent or mixture of solvents can be used in the invention process, hydroxylic solvents are particularly suitable. These include alcohols, glycols and carboxylic acids (for example, butanol, ethylene glycol and acetic acid), with water being particularly preferred from the standpoints of economics and ease of separation of products from the reaction mixture.

The improved process is carried out at 80°–120° C., preferably at the reflux temperature of the reaction mixture. When water is used as the solvent, water being the preferred solvent, the process is carried out at about 100° C. At this temperature the products are readily formed and then removed from the vapor phase. Subatmospheric or superatmospheric pressures can be used if lower or higher temperatures, respectively, are desired for reaction and removal of products.

Mercury must be present throughout the reaction (dehydration) as soluble mercury ions and as solid (insoluble) mercuric oxide (HgO). The rate of reaction depends primarily on the concentration of mercury ions. The soluble mercury salt employed as the catalyst must be highly dissociated, particularly under the preferred reaction conditions. Useful mercury salts include salts of organic carboxylic acids, such as the formate, acetate and succinate, and salts of inorganic oxyacids, such as the sulfate, nitrate, perchlorate and fluoroborate. Mercuric chloride can be used but it is less soluble and less dissociated in hydroxylic solvents. Preferred are the mercury salts of strong oxyacids, with mercuric sulfate and mercuric nitrate being particularly useful. Insoluble or poorly dissociated mercury salts, such as the cyanide, iodide or phosphate, should not be used.

As indicated above solid mercuric oxide must be present during the reaction; lower rates of reaction and/or lower yields are obtained when it is absent. The effect of the solid mercuric oxide is not catalytic, however, since the reaction rate does not depend on the amount present.

The pH of the reaction medium during the carrying out of the invention process is 4 to 7, preferably 5 to 6, measured in an aqueous system. The preferred pH is that of a solution of mercuric sulfate containing solid mercuric oxide. At a very low pH 1-butene-3,4-diol is converted to undesirable carbonyl compounds, vinyl ethers and polymeric materials. At a basic pH little if any 2,5-dihydrofuran is formed.

It is preferred to remove the 2,5-dihydrofuran from the reaction mixture as rapidly as it is formed to inhibit its oxidation to furan, with accompanying conversion of mercury ions to free mercury. Metallic mercury so produced can be removed and oxidized to mercuric oxide which is then returned to the system. The preferred method of removing 2,5-dihydrofuran is by distillation, since this compound forms a low boiling azeotrope with water. Other procedures can be employed, for example, extraction by means of an immiscible extractant; such extractants include alkylated benzenes, for example, toluene or xylene.

In carrying out the improved process of this invention it is preferred that the concentration of 1-butene-3,4-diol be less than about 75%, by weight, in the dissociating solvent to obtain better yields of 2,5-dihydrofuran and less by-product divinyldioxanes and ether-containing oligomers. Generally, to maximize yields, the concentration of diol is about 1 to 50%, preferably about 1 to 25%.

Although the above description of the process of this invention is directed to the preparation of 2,5-dihydrofuran from 1-butene-3,4-diol, the process can be carried out on mixtures of 1-butene-3,4-diol and 2-butene-1,4-diol and on 2-butene-1,4-diol itself since, under the conditions of the reaction, 2-butene-1,4-diol is isomerized to 1-butene-3,4-diol. It is preferred, however, to use the 3,4-diol or a mixture of 3,4-diol and 1,4-diol as the starting material. The examples which follow, except for Example 4, were carried out using 85/15, by weight, mixtures of these two diols. In Example 4 an 85/15, by weight, mixture of 1-butene-3,4-diol and 1,2-butanediol was used. Although the butanediol may provide its own reaction products when present while carrying out the process of the invention, it does not form 2,5-dihydrofuran and, from that standpoint, may be considered as an inert material and, therefore, was not included in the calculation of the yield of 2,5-dihydrofuran in Example 4.

EXAMPLE 1

A two-liter flask was charged with 20 g of butenediol (85/15, by weight, mixture of 1-butene-3,4-diol and 2-butene-1,4-diol), 3 g of mercuric oxide, 0.3 g of concentrated nitric acid and 200 cc of water. The flask was fitted with a simple still head and heated so that slow distillation of water (3–5 cc/hour) took place. After 30, 60, 120 and 480 minutes the liquid in the receiver flask was assayed by the following procedure.

A weighed aliquot of toluene was added to the material in the receiver flask and the relative volumes of the two layers were measured. The water layer was then saturated with sodium chloride and the organic layer was assayed by glpc (gas liquid phase chromatography) for 2,5-dihydrofuran, crotonaldehyde and divinyldioxanes using toluene or xylene as an internal standard.

These analyses were then corrected for the organic materials in the aqueous layer using independently-determined partition coefficients. At the end of the run a weighed amount of 1,6-hexanediol was added to the reaction flask and the amount of diols remaining therein was determined by glpc assay of the aqueous reaction mixture on a concentrated aliquot. From these data were derived diol conversions, overall yields of volatiles and diol concentrations as a function of time.

It was determined that:
(a) after 30 minutes 4 g of 2,5-dihydrofuran containing some divinyldioxanes was obtained,
(b) after 60 minutes 9 g of 2,5-dihydrofuran containing some divinyldioxanes was obtained,
(c) after 120 minutes 15.8 g of 2,5-dihydrofuran containing some divinyldioxanes was obtained, and
(d) after 480 minutes 90% of the diol had been converted, with a 68% yield of 2,5-dihydrofuran and a 22% yield of divinyldioxanes.

The rate of formation of 2,5-dihydrofuran in this example represents about a 20-fold increase over that obtained using mercuric acetate in the absence of mercuric oxide.

Using the general procedure of this example with a mixture of 100 g of 2-butene-1,4-diol, 8 g of mercuric oxide and 900 g of water, no 2,5-dihydrofuran was formed after 3.5 hours and the diol was substantially unchanged. Addition of 5 g of succinic acid initiated production of 2,5-dihydrofuran (62.5% yield in 32 hours), thus demonostrating the need for both the soluble mercury salt and the insoluble mercuric oxide in the process of this invention.

EXAMPLES 2–9

In Examples 2–9 the conversion of mixed butenediols (as described in Example 1 except for Example 4 wherein the 1-butene-3,4-diol contained 15 wt% of 1,2-butanediol) to 2,5-dihydrofuran was effected in a reactor which permitted continuous feed of reactants and withdrawal of products. The assembly included a flask equipped with a stirrer, thermometer, inlet for injection of butanediol(s) and stillhead with condenser for removal of volatiles. The flask and contents were maintained in a heating bath. The reactor was charged with 200–500 cc of water and the mercury catalyst described below. In Examples 2–6, 8 and 9 the soluble mercury salt was generated in situ, by the addition of acid to the mixture, from the excess of mercuric oxide used. The temperature of the reaction mixture was adjusted so that a slow distillation of water (2–4 g/hour) into the receiver was maintained. The diol, either neat or in aqueous solution, was injected so that the rate of production of volatile products equaled the molar rate of injection of diol. The selectivity to 2,5-dihydrofuran was evaluated under these steady state conditions. The overall yield of 2,5-dihydrofuran was determined by measuring the concentration thereof in the distillate after injection of diols was stopped. The residual solution was then assayed for unconverted diols and soluble mercury salts. The data for Examples 2–9 are tabulated in the following table, among with a comparison run carried out with mercuric acetate in the absence of mercuric oxide.

| Ex. | Water (cc) | Catalyst | % Productivity[a] | % Selectivity[b] | % Yield[c] |
|---|---|---|---|---|---|
| 2 | 100 | 10g HgO/1g HNO$_3$ | 48.7 | 0.88 | 81 |
| 3 | 200 | 20g HgO/2g HNO$_3$ | 47.1 | 0.89 | 78 |
| 4 | 200 | 20g HgO/2g HNO$_3$ | 49.0 | 0.92 | 75.2 |
| 5 | 500 | 50g HgO/5g HNO$_3$ | 49.0 | 0.88 | 80.5 |
| 6 | 200 | 40g HgO/2g HNO$_3$ | 46.9 | 0.89 | 79 |
| 7 | 200 | 20g HgO/1.6g Hg(BF$_4$)$_2$ | 57.0 | 0.92 | 75 |
| 8 | 200 | 20g HgO/0.9g HCl | 21.4 | 0.78 | 68 |
| 9 | 200 | 20g HgO/2g H$_2$SO$_4$ | 41.4 | 0.92 | 74.7 |
| — | 500 | 5g Hg(OAc)$_2$ | 2.4 | 0.69 | 66.7 |

[a] g of diol consumed/l of solution/hour
[b] g of 2,5-dihydrofuran formed/g of volatiles formed
[c] moles of 2,5-dihydrofuran formed/mole of diol consumed Examples 2–9 show that the rate of production (productivity) of 2,5-dihydrofuran in terms of space/time yield is independent of reactor volume but dependent on the ionization of mercuric salt, since the rate increased by a factor of 20 in going from Hg(OAc)$_2$ to Hg(NO$_3$)$_2$. The rate is substantially independent of the amount of mercury present as solid mercuric oxide.

BEST MODE FOR CARRYING OUT THE INVENTION

The best mode presently contemplated for the practice of this invention involves the general procedure of Examples 2–9, using mercuric oxide and the mercuric salt of a strong oxygen-containing inorganic acid.

INDUSTRIAL APPLICABILITY

Furan compounds are well established in industrial importance. Tetrahydrofuran (obtained by hydrogenation of furan or dihydrofuran) is a solvent for polyvinyl chloride and for inks and adhesives. Furan and di- and tetrahydrofuran are intermediates which are used in the production of various compounds, for example, chlorobutanol, butyrolacetone, succinic acid and pyrrolidine.

I claim:

1. Improved process for preparing 2,5-dihydrofuran by the dehydration of 1-butene-3,4-diol in the presence of a soluble mercury salt as catalyst in a dissociating solvent at a neutral or acidic pH at an elevated temperature, the improvement characterized in that the dehydration is carried out at a pH of 4 to 7 at 80°–120° C. in the presence of solid mercuric oxide.

2. Process of claim 1 carried out continuously.

3. Process of claim 1 carried out batchwise.

4. Process of claim 1 wherein the dissociating solvent is a hydroxylic solvent.

5. Process of claim 4 wherein the hydroxylic solvent is water.

6. Process of claim 5 wherein the temperature is reflux temperature.

7. Process of claim 1 wherein the soluble mercury salt catalyst is formed in situ from some of the solid mercuric oxide.

8. Process of claim 7 wherein nitric acid is used to form the soluble mercury salt catalyst from some of the solid mercuric oxide.

9. Process of claim 7 wherein sulfuric acid is used to form the soluble mercury salt catalyst from some of the solid mercuric oxide.

* * * * *